(12) United States Patent
Seymour et al.

(10) Patent No.: US 9,782,091 B2
(45) Date of Patent: Oct. 10, 2017

(54) OPTO-ELECTRICAL DEVICE FOR ARTIFACT REDUCTION

(75) Inventors: John P. Seymour, Ann Arbor, MI (US);
Jongeun Jeon, Ann Arbor, MI (US);
Nicholas Hewitt, Chelsea, MI (US);
Abeer Khurram, Ypsilanti, MI (US)

(73) Assignee: NEURONEXUS TECHNOLOGIES, INC., Ann Arbor, TX (US)

( * ) Notice: Subject to any disclaimer, the term of this patent is extended or adjusted under 35 U.S.C. 154(b) by 417 days.

(21) Appl. No.: 13/557,516

(22) Filed: Jul. 25, 2012

(65) Prior Publication Data

US 2013/0030275 A1 Jan. 31, 2013

Related U.S. Application Data

(60) Provisional application No. 61/511,358, filed on Jul. 25, 2011.

(51) Int. Cl.
*A61N 1/00* (2006.01)
*A61B 5/04* (2006.01)
*A61B 5/00* (2006.01)
*A61N 5/06* (2006.01)
*A61N 1/05* (2006.01)

(52) U.S. Cl.
CPC ........ *A61B 5/04001* (2013.01); *A61B 5/6847* (2013.01); *A61N 5/0622* (2013.01); *A61B 5/6868* (2013.01); *A61N 1/0534* (2013.01); *A61N 2005/0612* (2013.01); *Y10T 29/49826* (2015.01); *Y10T 29/49886* (2015.01)

(58) Field of Classification Search
CPC .. A61N 1/0534; A61N 1/0529; A61N 1/0456; A61N 5/0622; A61B 5/04001; A61B 5/4064

USPC ........ 600/372–373, 377–378, 393, 395–396, 600/544–545; 607/2, 45, 88, 93, 607/115–116, 118
See application file for complete search history.

(56) References Cited

U.S. PATENT DOCUMENTS 3,628,017 A 12/1971 Lerner
4,717,581 A * 1/1988 Robblee .................. A61N 1/05
427/126.5

(Continued)

FOREIGN PATENT DOCUMENTS

WO 2008/089003 7/2008
WO 2009/072123 6/2009
(Continued)

OTHER PUBLICATIONS

Paik et al. "Roughened polysilicon for low impedance microelectrodes in neural probes" Journal of Micromechanics and Microengineering Issue 13 (2003) pp. 373-379.*
(Continued)

*Primary Examiner* — Joseph Stoklosa
*Assistant Examiner* — Brian M Antiskay
(74) *Attorney, Agent, or Firm* — Haynes and Boone, LLP; Taylor Merritt Meacham (57) ABSTRACT

An optical electrode having a plurality of electrodes, including a recording electrode having a roughened surface and an optical light source configured to emit light, wherein at least a portion of the light impinges on the recording electrode. Also disclosed are methods of producing an optical electrode and an opto-electronic neural interface system.

17 Claims, 12 Drawing Sheets

(56) References Cited

U.S. PATENT DOCUMENTS

| | | | |
|---|---|---|---|
| 5,629,009 A | 5/1997 | Laurencin et al. | |
| 5,683,443 A * | 11/1997 | Munshi | A61N 1/0565 607/119 |
| 6,238,994 B1 | 5/2001 | Derderian et al. | |
| 6,294,074 B1 | 9/2001 | Lin et al. | |
| 7,310,546 B2 | 12/2007 | Prass | |
| 7,375,870 B2 | 5/2008 | Schorpp | |
| 7,781,195 B1 | 8/2010 | Heller et al. | |
| 7,887,681 B2 * | 2/2011 | Zhou | A61N 1/05 204/292 |
| 7,955,889 B1 | 6/2011 | Yang et al. | |
| 8,005,526 B2 | 8/2011 | Martin et al. | |
| 8,355,793 B2 * | 1/2013 | Dadd | A61N 1/36032 607/57 |
| 2002/0183682 A1 | 12/2002 | Darvish et al. | |
| 2003/0147958 A1 | 8/2003 | Ahn et al. | |
| 2004/0111139 A1 | 6/2004 | McCreery | |
| 2006/0024359 A1 | 2/2006 | Walker et al. | |
| 2008/0208283 A1 * | 8/2008 | Vetter | A61N 1/0539 607/45 |
| 2008/0249391 A1 * | 10/2008 | Moxon et al. | 600/373 |
| 2009/0054954 A1 | 2/2009 | Foley et al. | |
| 2009/0099038 A1 | 4/2009 | Deisseroth et al. | |
| 2009/0118800 A1 | 5/2009 | Deisseroth et al. | |
| 2009/0292325 A1 | 11/2009 | Cederna et al. | |
| 2010/0015095 A1 | 1/2010 | Pan et al. | |
| 2010/0049263 A1 | 2/2010 | Reeve | |
| 2010/0137960 A1 * | 6/2010 | Moffitt et al. | 607/116 |
| 2010/0161017 A1 | 6/2010 | Choi et al. | |
| 2010/0190229 A1 | 7/2010 | Zhang et al. | |
| 2010/0191308 A1 | 7/2010 | Meister | |
| 2010/0211172 A1 | 8/2010 | Bellamkonda et al. | |
| 2010/0268150 A1 | 10/2010 | Mohanty et al. | |
| 2011/0021970 A1 | 1/2011 | Vo-Dinh et al. | |
| 2011/0087126 A1 | 4/2011 | Zorzos et al. | |
| 2011/0093052 A1 | 4/2011 | Anderson et al. | |
| 2011/0105998 A1 | 5/2011 | Zhang et al. | |
| 2011/0112591 A1 | 5/2011 | Seymour et al. | |
| 2011/0144566 A1 | 6/2011 | Dacey, Jr. et al. | |
| 2011/0172736 A1 | 7/2011 | Gefen et al. | |
| 2011/0311489 A1 | 12/2011 | Deisseroth et al. | |
| 2011/0318775 A1 | 12/2011 | Mercola et al. | |
| 2012/0035725 A1 | 2/2012 | Gefen et al. | |
| 2012/0035726 A1 | 2/2012 | Gross et al. | |
| 2012/0101356 A1 * | 4/2012 | Kim | A61B 5/04842 600/378 |
| 2012/0130302 A1 | 5/2012 | Wrobel et al. | |
| 2012/0149052 A1 | 6/2012 | Grohovaz et al. | |
| 2013/0030352 A1 | 1/2013 | Seymour et al. | |
| 2013/0079615 A1 * | 3/2013 | Yoon | A61B 5/04001 600/377 |
| 2013/0090542 A1 * | 4/2013 | Kipke | A61B 5/04001 600/377 |
| 2013/0131485 A1 * | 5/2013 | Oh | A61N 1/0529 600/393 |
| 2014/0350375 A1 * | 11/2014 | Wolfe | A61B 5/0084 600/377 |

FOREIGN PATENT DOCUMENTS

| | | |
|---|---|---|
| WO | 2009/124220 | 8/2009 |
| WO | 2009/131837 | 10/2009 |
| WO | 2010/029297 | 3/2010 |
| WO | 2010/056970 | 5/2010 |
| WO | 2010/105728 | 9/2010 |
| WO | 2011/057137 | 5/2011 |
| WO | 2011/057276 | 5/2011 |
| WO | 2012/052727 | 4/2012 |
| WO | 2012/061676 | 5/2012 |
| WO | 2012/061679 | 5/2012 |
| WO | 2012/061688 | 5/2012 |
| WO | 2012/061744 | 5/2012 |
| WO | 2012/075337 | 6/2012 |
| WO | 2013/016391 | 1/2013 |
| WO | 2013/016392 | 1/2013 |

OTHER PUBLICATIONS

Light-Induced Artifact, Retrieved from the Internet on Jun. 21, 2012 <URL: http://www.openoptogenetics.org/index.php?title=Light-Induced_Artifact>.

Shimada, "Neural Function Observation with Microelectrode Array," NIT Technical Review, Aug. 2009, vol. 7, No. 8, pp. 1-5.

Pachnis, Neutralisation of myoelectric interference from recorded nerve signals using models of the electrode impedance, University College London Department of Electronic and Electrical Engineering, Sep. 2010.

Aravanis et al., "An optical neural interface: in vivo control of rodent motor cortex with integrated fiberoptic and optogenetic technology," Journal of Neural Engineering, 2007, vol. 4, pp. S143-S156.

Bernstein et al., "Prosthetic systems for therapeutic optical activation and silencing of genetically-targeted neurons," Proc Soc Photo Opt Instrum Eng, 2008, 6854, 68540H.

Royer et al., "Light activation and detection of hippocampal neurons in the behaving rat," Presentation Abstract, Neuroscience, Nov. 17, 2008.

Dias et al., "New dry electrodes based on iridium oxide (IrO) for non-invasive biopotential recordings and stimulation," Sensors and Actuators A: Physical, 2010, vol. 164, pp. 28-34.

Adamantidis et al., "Neural substrates of awakening probed with optogenetic control of hypocretin neurons," Nature, Nov. 2007, vol. 450, pp. 420-425.

Arenkiel et al., "In Vivo Light-Induced Activation of Neural Circuitry in Transgenic Mice Expressing Channelrhodopsin-2," Neuron, Apr. 2007, vol. 54, pp. 205-218.

Farah et al., "Patterned Optical Activation of Retinal Ganglion Cells," Proceedings of the 29th Annual International Conference of the IEEE EMBS, Cité Internationale, Lyon, France, Aug. 23-26, 2007, pp. 6368-6370.

Froehlich et al., "Messung Und Analyse Monophasischer Aktionspotentiale Mit Hilfe Fraktal Beschichteter Elektroden—Teil I," Biomedizinsche Technik, Fachverlad Schiele Und Schoen GmbH, Berlin, DE, vol. 40, No. 6, Jun. 1, 1995, pp. 154-159.

Gradinaru et al., "Targeting and Readout Strategies for Fast Optical Neural Control In Vitro and In Vivo," The Journal of Neuroscience, Dec. 2007, vol. 27(52), pp. 14231-14238.

Lu Y et al: "Electrodeposited polypyrrolejcarbon nanotubes composite films electrodes for neural interfaces", Biomaterials, Elsevier Science Publishers BV., Barking, GB, vol. 31, No. 19, Jul. 1, 2010, pp. 5169-5181.

PCT/US2012/048073 International Search Report and Written Opinion dated Oct. 17, 2012 (11 pages).

PCT/US2012/048075 International Search Report and Written Opinion dated Nov. 21, 2012 (17 pages).

PCT/US2012/048076 International Search Report and Written Opinion dated Oct. 17, 2012 (8 pages).

Villalobos et al., "All-optical control of neuronal function via optical delivery of light-sensitive proteins and optogenetic stimulation," 2012 BiOs, SPRI Photonics West, 8207G-178, Session 7, p. 65.

Zhang et al., "A Microelectrode Array Incorporating an Optical Waveguide Device for Stimulation and Spatiotemporal Electrical Recording of Neural Activity," 31st Annual International Conference of the IEEE EMBS, Minneapolis, Minnesota, USA, Sep. 2-6, 2009, pp. 2046-2049.

Zhang et al., "Channelrhodopsin-2 and optical control of excitable cells," Nature Methods, Oct. 2006, vol. 3, No. 10, pp. 785-792.

Zhang et al., "Circuit-breakers: optical technologies for probing neural signals and systems," Neuroscience, Aug. 20007, vol. 8, pp. 577-581.

Zhang et al., "Integrated device for optical stimulation and spatiotemporal electrical recording of neural activity in light-sensitized brain tissue," J Neural Eng, Oct. 2009, vol. 6(5), pp. 1-24.

(56) References Cited

OTHER PUBLICATIONS

Zhang et al., "Multimodal fast optical interrogation of neural circuitry," Nature, Apr. 2007, vol. 446, pp. 633-641.

* cited by examiner

OPTO-ELECTRICAL DEVICE FOR ARTIFACT REDUCTION

CROSS-REFERENCE TO RELATED APPLICATIONS

This application claims the benefit of U.S. Provisional Application No. 61/511,358 filed Jul. 25, 2011, which is incorporated herein by reference in its entirety.

FEDERALLY SPONSORED RESEARCH

This invention was made with government support under 1R43NS073185-01 awarded by National Institutes of Health, National Institute of Neurological Disorders and Stroke. The government has certain rights in the invention.

TECHNICAL FIELD

This invention relates generally to the neural device field, and more specifically to an improved opto-electrical device with artifact reduction in the neural device field.

BACKGROUND

One recent advance in neuroscience is the use of optogenetic tools to perturb neural circuits, particularly neural circuits with cell-type specificity. These optogenetic tools enable optical stimulation of neurons using light-sensitive ion channels (such as transfection occurring from viral vectors carrying opsins such as ChR2 or Halorhodopsin) for optical stimulation and neuromodulation applications. For example, a transfected neuron may be selectively activated or silenced as a result of exposure to a certain wavelength of light. Optogenetics allows experimenters or medical practitioners to use light stimulation to selectively excite neural channels and/or inhibit other neural channels with high precision.

However, in devices where neural sensing is combined with neural optical stimulation, the neural sensing elements experience increased noise and artifact from the photoelectrochemical (PEC) effect, also known as the Becquerel effect. The PEC effect results in artifacts of electrical signals that interfere with or obscure the recording of desired neural electrical signals, thereby interfering with the function and operation of neural optogenetic devices. Thus, there is a need in the neural device field to create an improved opto-electrical device with artifact reduction. This invention provides such an improved opto-electrical device.

SUMMARY

In one embodiment, the invention provides an optical electrode having a plurality of electrodes, including a recording electrode having a roughened surface and an optical light source configured to emit light, wherein at least a portion of the light impinges on the recording electrode.

In another embodiment, the invention provides a method of producing an optical electrode with a reduced photoelectrochemical artifact. The method includes steps of coupling a plurality of electrodes to a carrier, the plurality of electrodes having at least one recording electrode; providing a roughened surface on the at least one recording electrode; and coupling an optical light source to the carrier, the optical light source being configured to emit light and wherein at least a portion of the light impinges on the at least one recording electrode.

In yet another embodiment, the invention provides an opto-electronic neural interface system. The system includes an optical electrode having a plurality of electrodes, including a recording electrode having a roughened surface, and an optical light source configured to emit light, wherein at least a portion of the light impinges on the recording electrode; an electrical subsystem in communication with the plurality of electrodes; and an optical subsystem in communication with the optical light source.

Other aspects of the invention will become apparent by consideration of the detailed description and accompanying drawings.

BRIEF DESCRIPTION OF THE DRAWINGS

FIGS. 5A and 5B show electrical recordings from electrodes depicting the artifact stabilization time for electrodes that are smooth (uncoated; FIG. 5A) or roughened (treated with PEDOT at 3 $nC/\mu m^2$; FIG. 5B).

FIGS. 6A and 6B show electrical recordings from electrodes depicting the artifact dissipation time for electrodes that are smooth (uncoated; FIG. 6A) or roughened (treated with PEDOT at 1 $nC/\mu m^2$; FIG. 6B).

DETAILED DESCRIPTION

Before embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
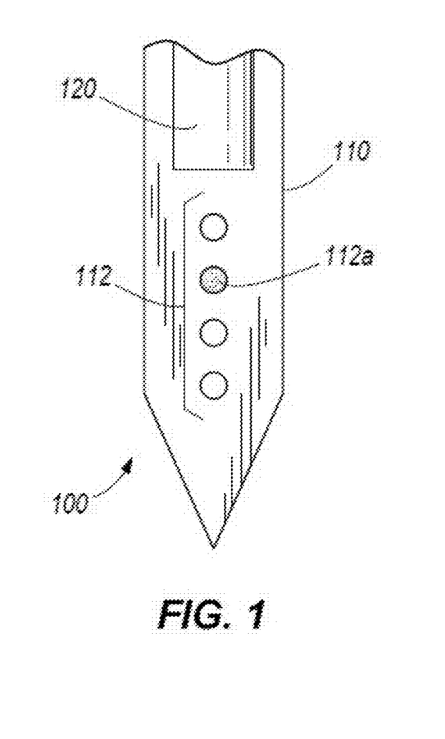
FIG. 1 is a side-view schematic of one embodiment of an optical electrode.
Figure 2:
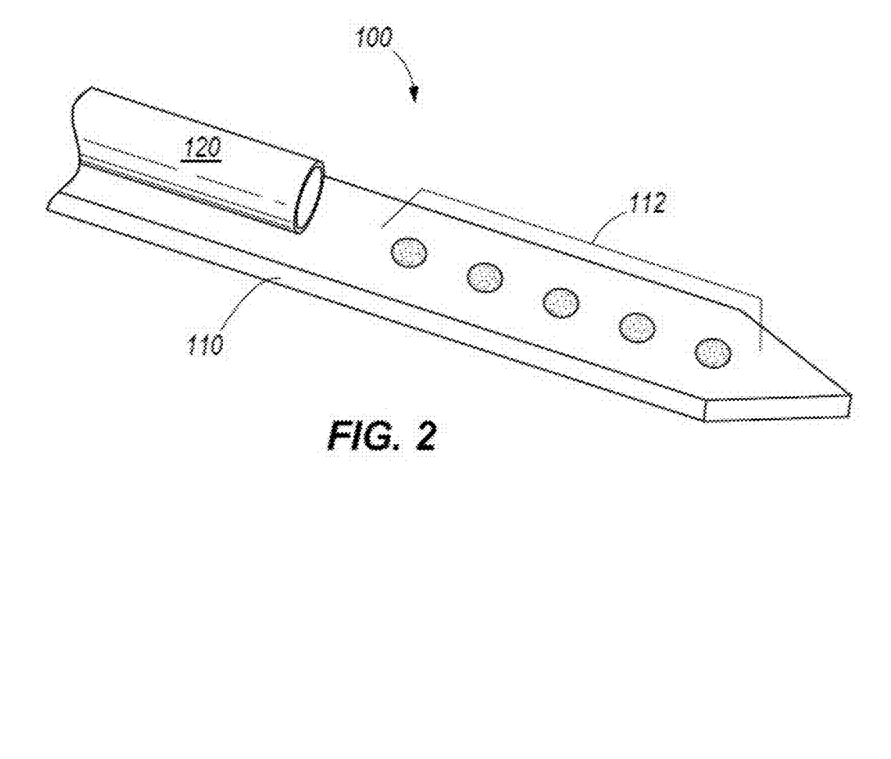
FIG. 2 is a perspective view schematic of another embodiment of an optical electrode.

As shown in FIGS. 1 and 2, an opto-electrical device 100, or "optrode" or "optical electrode," according to one embodiment includes: a carrier 110 insertable in tissue; an electrode array 112 disposed on the carrier 110 and having a plurality of electrodes including at least one recording electrode site having a roughened surface 112a, the recording electrode configured to 'record' or sense electrical signals from its surroundings; and an optical light source 120 configured to illuminate selectively-targeted regions of the tissue. The opto-electrical device 100 may be used in applications with optogenetic techniques involving optical stimulation patterns of tissue and neural recording capabilities. In various embodiments, the opto-electrical device 100 is insertable or implantable in neural tissue (e.g. the brain), but may additionally and/or alternatively be used with other suitable tissues.

The carrier 110 functions to provide structural support for the electrode array 112 and, in some cases, for insertion and/or implantation of the opto-electrical device 100 into tissue. The carrier 110 may be planar, cylindrical, or other suitable shapes. In some embodiments, the carrier 110 may be similar to that in the neural device described in U.S. Patent Application number 2011/0112591 (hereinafter referred to as the '591 publication) entitled "Waveguide neural interface device," which is incorporated in its entirety by this reference. However, other suitable carriers 110 may be used. The carrier 110 may be made of other suitable materials or combination of materials, including those listed in the '591 publication or in US 2011/0093052 (hereinafter referred to as the '052 publication) entitled "Neural Interface System," which is incorporated in its entirety by this reference. In some embodiments, the waveguide 120 may serve as a carrier with an electrode array 112 being associated with the waveguide 120. In various embodiments, optrodes such as those disclosed herein may be used with a neural interface system, such as disclosed in the '052 publication.

In certain embodiments the opto-electrical device 100 is part of a neural interface system 1000, which may include an electrical subsystem 1100, an optical subsystem 1200, and a controller 2000. The electrical subsystem 1100 functions to operate with the electrode array 112, for example when the electrode array 112 is implanted into a subject 1500 (FIG. 13). The subject 1500 may include any number of animals into which the opto-electrical device 100 may be implanted and with which the neural interface system 1000 may be employed, including without limitation rodents (e.g. rats, mice, rabbits, etc.) and primates (e.g. humans, monkeys, etc.).

The controller 2000 may control one or both of the electrical subsystem 1100 and the optical subsystem 1200 to carry out the functions of the neural interface system 1000 such as those disclosed herein. The electrical subsystem 1100, optical subsystem 1200, and controller 2000 may be integrated into a single unit or may be separate units, and each may be external to the subject 1500 or may be part of an implanted device. Each of the electrical subsystem 1100, optical subsystem 1200, and controller 2000 may include a processor, memory, storage, amplifiers, A/D convertors, input/output mechanisms, and communication mechanisms, including capabilities for wired and/or wireless communications within the components of the system 1000 and between the system 1000 and external computers and networks.

The electrical subsystem 1100 includes at least one of several variations of suitable electronic subsystems to operate with (e.g. sense electrical signals at) the electrode array 112 or combinations thereof. The electrical subsystem 1100 may be a printed circuit board with or without onboard amplifier or integrated circuits and/or on-chip circuitry for signal sensing and/or conditioning and/or stimulus genera-tion, an Application Specific Integrated Circuit (ASIC), a multiplexer chip, a buffer amplifier, an electronics interface, a pulse generator (which produces signals such as a high-frequency, pulsed electric current, and which in certain embodiments may be implantable), a power supply (which in various embodiments can include an implantable rechargeable battery), integrated electronics for signal processing of the input (recorded) or output (stimulation) signals (either of which may be processed in real time), other suitable electrical subsystem, or combinations thereof, as disclosed in the '052 publication.

The optical subsystem 1200, which is in communication with the optical light source 120, includes power and control units to control the light source 120 in order to generate light pulses of suitable wavelength, duration, intensity, and pulse shape. The optical light source 120 functions to illuminate surrounding tissue and stimulating targeted tissue. In some embodiments, the optical light source 120 is coupled to the carrier such that the light from the optical light source 120 has an angle of incidence that is minimal relative to the surface of the recording electrode sites (e.g. less than normal incidence). In one embodiment, the optical light source 120 provides illumination approximately parallel to the surface of the recording electrode site. However, the optical light source 120 may be positioned in other suitable locations relative to the electrode site surface.

In various embodiments, the optical light source 120 may include one or more LEDs or a waveguide, where the LEDs may be included on the carrier 110 (e.g. in the vicinity of the electrode array 112). Alternatively, the waveguide may be coupled to a light source that is nearby (e.g. part of the implantable device) or remote (e.g. part of an external component associated with the implantable device). The light source to which the waveguide is coupled may be one or more LEDs, a laser, or other suitable light source (e.g. as disclosed in the '591 publication), and in various embodiments is controlled by the optical subsystem 1200. The optical light source 120 can have a number of configurations relative to the electrode array 112, e.g. as shown in the '591 publication, and as a result light emitted from the optical light source 120 may impinge on one or more electrodes in the electrode array 112 in a direction that is parallel, perpendicular, or at other angles relative to the surface on which the plurality of electrodes is disposed.

The electrode array 112 functions to electrically communicate with its surroundings. In various embodiments, the electrode array 112 can include one or more recording electrode sites that sense and record neural signals in surrounding tissue, and in some embodiments the electrode array 112 may additionally and/or alternatively include stimulation electrode sites. The electrode array 112 may be arranged longitudinally along (e.g. as shown in FIGS. 1 and 2) and/or circumferentially around a cylindrical carrier 110, along a face or edge of a planar carrier 110, or in other suitable arrangements on the carrier 110. The opto-electrical device 100 may further include an optical light source 120 such as a waveguide arranged proximate to the electrode array 112, as shown in FIGS. 1 and 2 or as shown and described in the '591 publication. In various embodiments, the electrode sites may include conductive metal (e.g. gold, platinum, iridium, platinum-iridium, titanium nitride, iridium oxide, etc.) and may be formed by microfabrication techniques, such as thin-film or other microelectromechanical systems (MEMS) manufacturing processes.

A metal electrode that is "smooth" (not roughened) in general has an average roughness ($R_a$) of less than 10 nm (average of series of maximum and minimum height measurements). It is demonstrated herein that treatments that increase the average roughness of a recording electrode (or a material applied thereto, FIG. 3) to greater than about 10 nm have the effect of reducing the photoelectrochemical artifact. According to various embodiments, a roughened electrode 112a has an average roughness of greater than 10 nm, greater than 20 nm, greater than 30 nm, greater than 50 nm, or greater than 100 nm. Average roughness ($R_a$) is an arithmetic average of absolute values of vertical deviations of height on a surface, expressed in units of height (e.g. nanometers).

Figure 3:
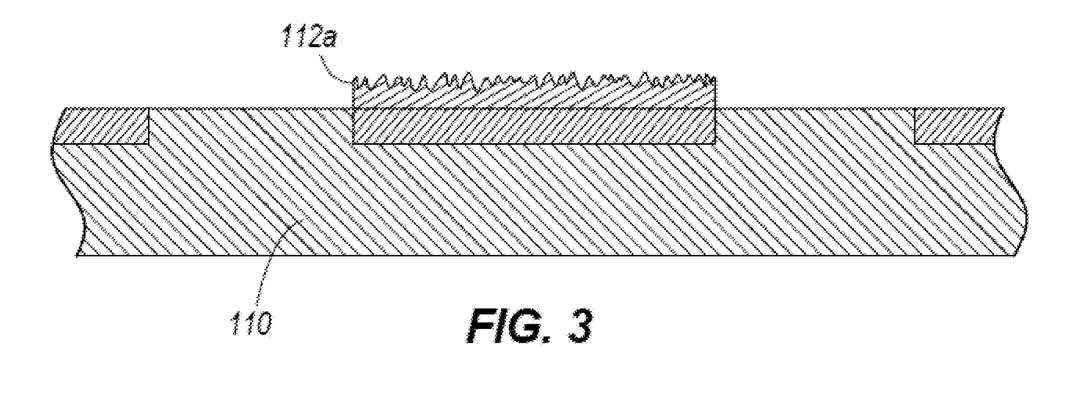
FIG. 3 is a sectional view of an embodiment of an electrode with roughening material applied to the electrode surface.
Figure 4:
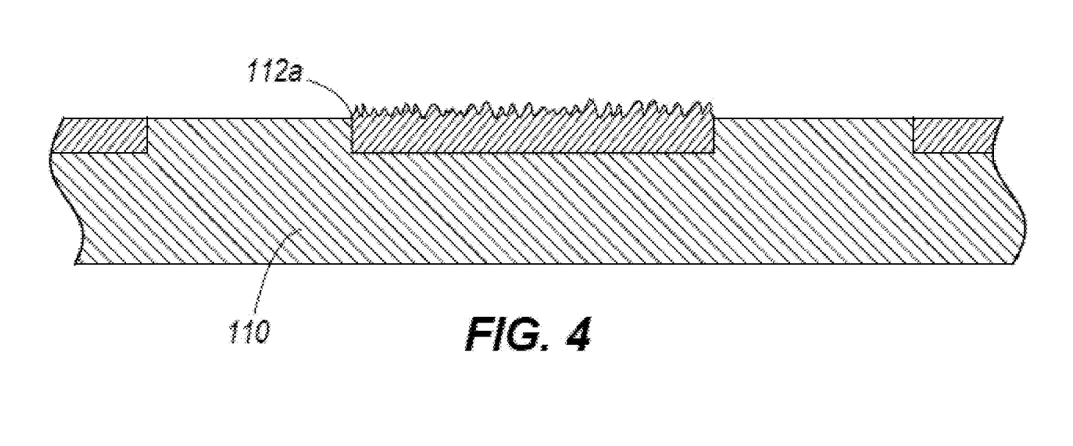
FIG. 4 is a sectional view of another embodiment of a roughened electrode.

In various embodiments, one or more recording electrodes 112a in the electrode array 112 may have a roughened surface (FIGS. 1, 3, and 4). The roughening can take a number of forms and may produce a tortuous surface such as with recesses, pores, and/or other surface modifications that reduce the smoothness and increase the effective surface area of the electrode surface. The roughened surface may have a pattern (e.g. grooves, cross-hatching, regularly-spaced protrusions or depressions, etc.) or may be essentially random. The roughened surface 112a may be produced by applying a material (FIG. 3) to the electrode, by producing an electrode having a roughened surface as part of the electrode itself (FIG. 4), or a combination of methods. The material applied to the surface can include PEDOT/PSS (poly(3,4-ethylenedioxythiophene)/poly(styrene sulfonate), iridium oxide, or nanostructures (e.g. nanotubes, nanoparticles, nanospheres) made from a variety of materials. For example, glass or polystyrene nanospheres or microspheres may be applied to one or more electrodes on the electrode array 112 during microfabrication to form a highly dense pattern on the modified electrode array. In some embodiments, platinum may be applied to a surface using electrodeposition of Pt nanoparticles. In certain embodiments, the recording electrode and the roughened surface 112a may be substantially free of transparent and semi-transparent conductors such as indium-tin-oxide.

In one embodiment, polystyrene nanospheres were applied to an electrode surface producing feature sizes of at least 200 nm in height and an average roughness $R_a$ of 300 nm. In one particular embodiment in which 800 nm nanospheres were applied, $R_a$ was found to be 365±37 nm (average±standard error) and the RMS (root mean square) surface roughness was 368 nm. In various embodiments, a roughened electrode 112 has an RMS surface roughness of greater than 50 nm, greater than 100 nm, or greater than 200 nm.

In another embodiment, PEDOT/PSS was applied to a micromachined electrode (e.g. using techniques such as those in U.S. Pat. No. 8,005,526, which incorporated herein by reference) and the size of features was found to range from 50 nm-1000 nm and the $R_a$ was 700±243 nm for particular surfaces that were measured.

In still other embodiments iridium oxide can be applied to the recording electrode to roughen the surface, as shown in Dias et al. (2010, "New dry electrodes based on iridium oxide (IrO) for non-invasive biopotential recordings and stimulation," Sensors and Actuators A: Physical, 164:28-34; incorporated by reference herein). Iridium oxide can produce filamentous, globular, or other surface features with feature sizes of 10 nm or greater and average roughness $R_a$ values ranging from 27 nm to 183 nm.

According to further embodiments, the electrode surface may be roughened in one or more variations of surface modification steps. The electrode modification may include direct metal deposition (e.g., physical vapor deposition or PVD, sputtering, evaporation), electrochemical deposition from a solution, electrochemical activation (e.g. oxide growth), a sol-gel process, and/or micromachining and microfabrication techniques including the use of plasma etching (in which the exact chemistry depends on the type of metal in the electrode surface). Various parameters, such as duration, pressure, and temperature of deposition and other tools may also be adjusted to selectively modify the electrode site surfaces. However, other suitable methods of selectively depositing, forming, or machining a rough, tortuously textured conductive medium may be used. The electrode surface may be modified by micromachining or other suitable techniques to create a porous, discontinuous surface with a similarly tortuous electrical double layer. Furthermore, the electrode site surfaces may include materials that are naturally recessed and/or porous.

Each of the one or more roughened electrodes 112a, which are generally planar, has a geometric surface area based on its physical dimensions such as length, width, and/or diameter. On the other hand, each of the one or more roughened electrodes 112a has an effective surface area that is at least two to ten times greater than the geometric surface area of the same electrode, and in various embodiments is at least twenty, fifty, one hundred, or one thousand times greater than the geometric surface area of the same electrode.

When a roughened electrode surface is immersed in brain tissue or other electrolyte environments and subsequently exposed to light, the roughening reduces the electrical artifacts that occur due to the photoelectrochemical effect (also known as the Becquerel effect). As mentioned above, these electrical artifacts, which occur with use of conventional optrodes, may interfere with or obscure the recording of the desired neural signals. In one hypothesis, the photoelectrochemical effect is thought to begin with a photoelectric event in which photons cause emission of electrons upon striking a non-transparent metal surface. Many of these emitted electrons are thought to enter the surrounding environment, where they directly or indirectly interact with and disturb the electrical double layer (a double layer of charge that spontaneously forms at the interface between the electrode and surrounding electrolyte solution). According to this hypothesis, when many emitted electrons simultaneously interfere with the electrical double layer in a particular region, the synchronized interferences may be observed as an artifact of voltage fluctuation measured by an electronic amplifier connected to the electrode.

Without being limited by theory, the roughening may reduce the artifact due to the photoelectrochemical effect by increasing an effective surface area of the electrode and producing a lower surface charge density. The lower surface charge density may reduce the probability that an emitted electron will interact with a charge in the electrical double layer.

The following are examples in which it is demonstrated that roughening a recording electrode reduces the photoelectrochemical artifact that occurs when the electrode is placed in an electrolyte solution.

Figure 5A:
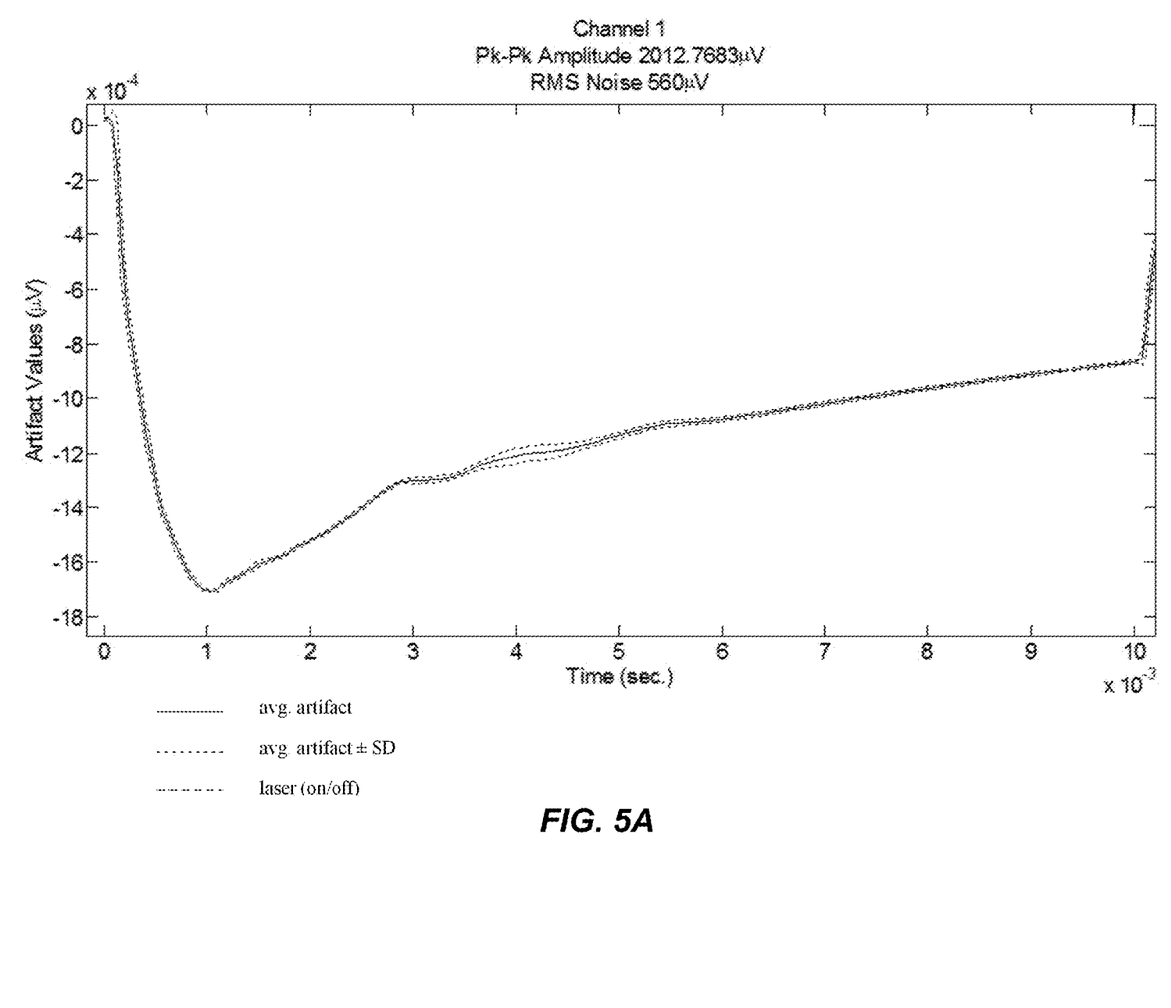
Figure 5B:
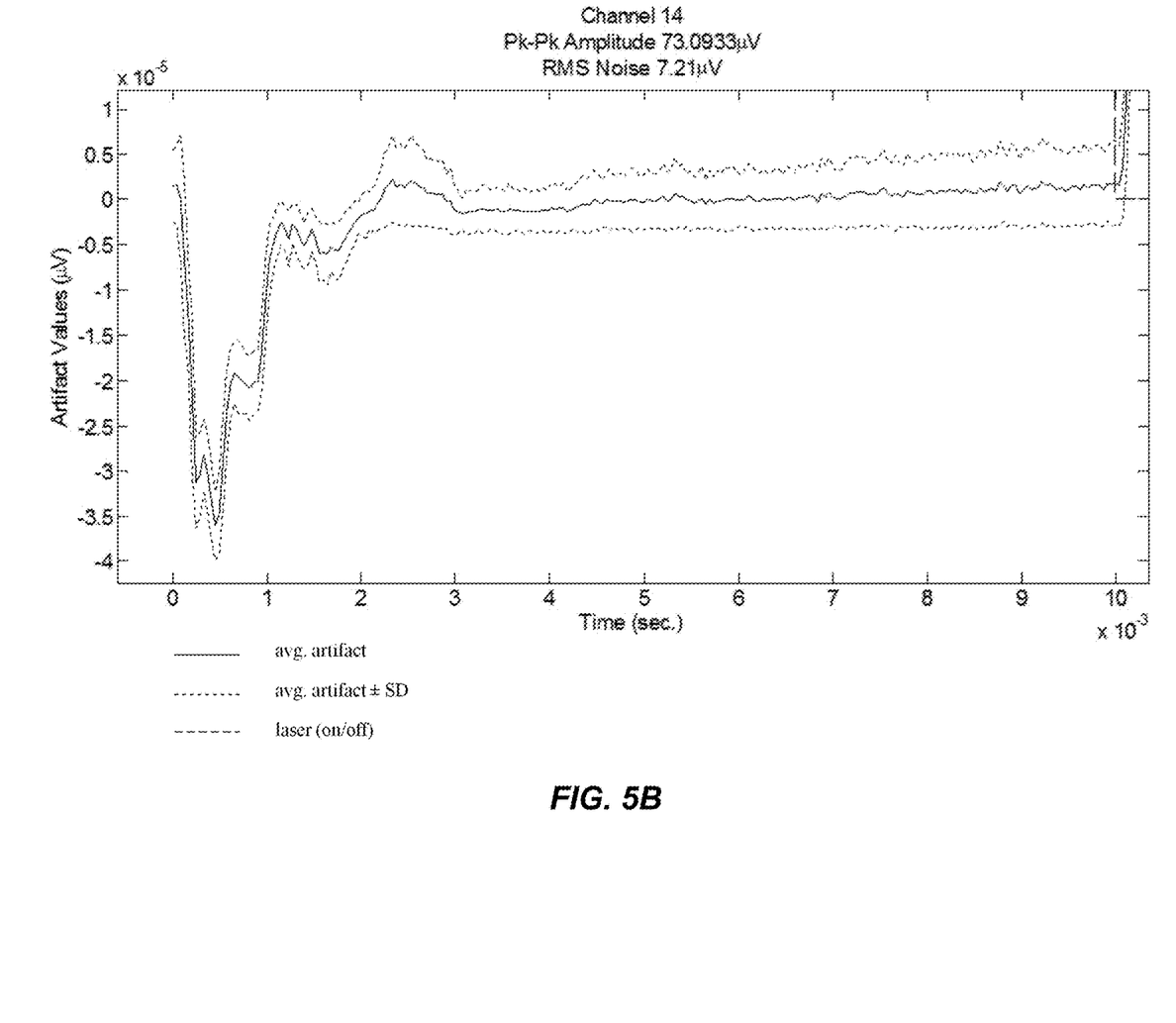
Figure 6A:
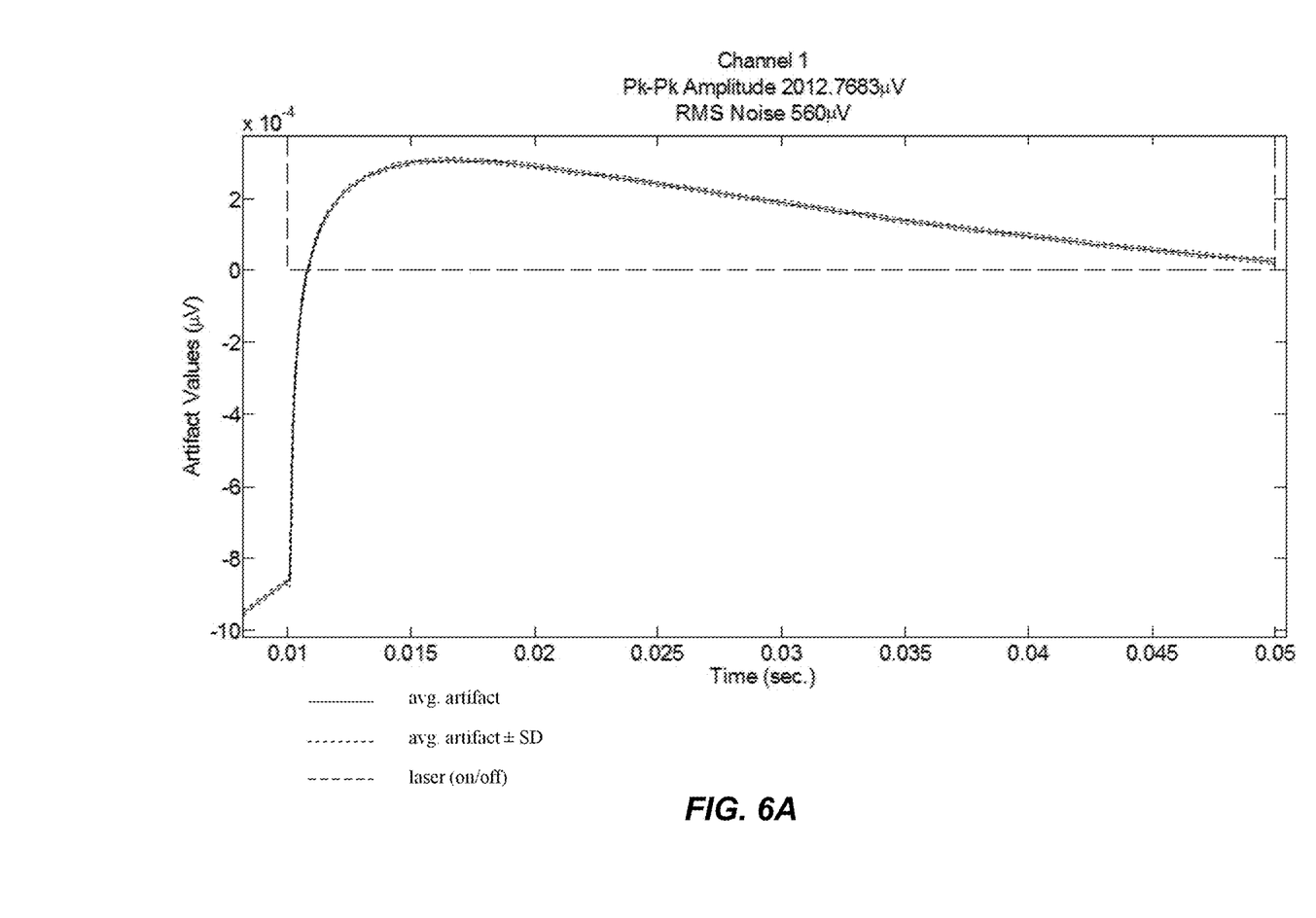
Figure 6B:
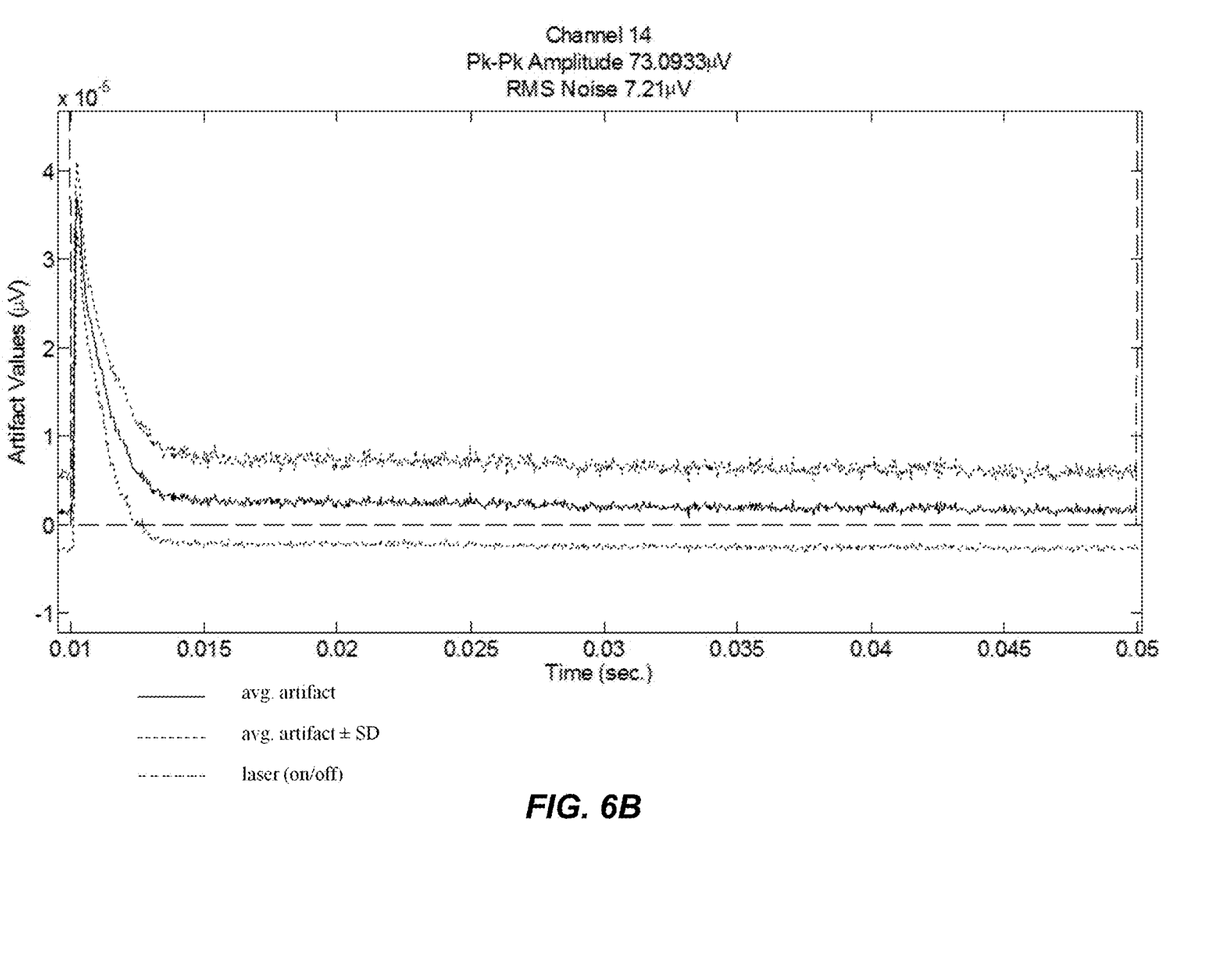

In one example, two groups of electrode sites were placed in an ionic solution of PBS 1× and electrical signals were recorded after being impinged with a laser diode: a first group in which the electrode sites were coated with PEDOT at 3 nC/$\mu m^2$ (FIG. 5B) or at 1 nC/$\mu m^2$ (FIG. 6B), and a second group in which the electrode sites were not substantially coated with PEDOT, such that the first group of electrode sites (FIGS. 5B, 6B) had surfaces substantially roughened compared to that of the second group of electrode sites (FIGS. 5A, 6A). As shown in FIGS. 5A and 5B, the signal from the roughened electrode sites (using nanosphere patterning) recorded significantly shorter artifact stabilization time than the unroughened electrode sites. As shown in FIGS. 6A and 6B, the signal from the roughened electrode sites recorded an artifact significantly smaller in amplitude than that from the unroughened electrode sites. Furthermore, after removal of the light source, in the signal from the roughened electrode sites the artifact dissipated as an inverted waveform, more quickly than in the signal from the unroughened electrode sites. Electrophysiologists may also easily filter out short-duration artifacts more readily than artifacts having a pulse-width similar to the physiological signal, e.g. the pulse-width of a single-cell action potentials.

In another example, a smaller electrode having a smaller recessed surface area (~177 µm$^2$) and a larger electrode having a larger recessed surface area (~703 µm$^2$) were placed in an ionic solution and illuminated with light incident approximately parallel to the electrode surface. Comparison of the signal recorded by the smaller electrode and the signal recorded by the larger electrode suggested that when light is incident on an electrode approximately parallel to the surface, then the surface area of the electrode is inversely proportional to the amplitude of the artifact.

Figure 7:
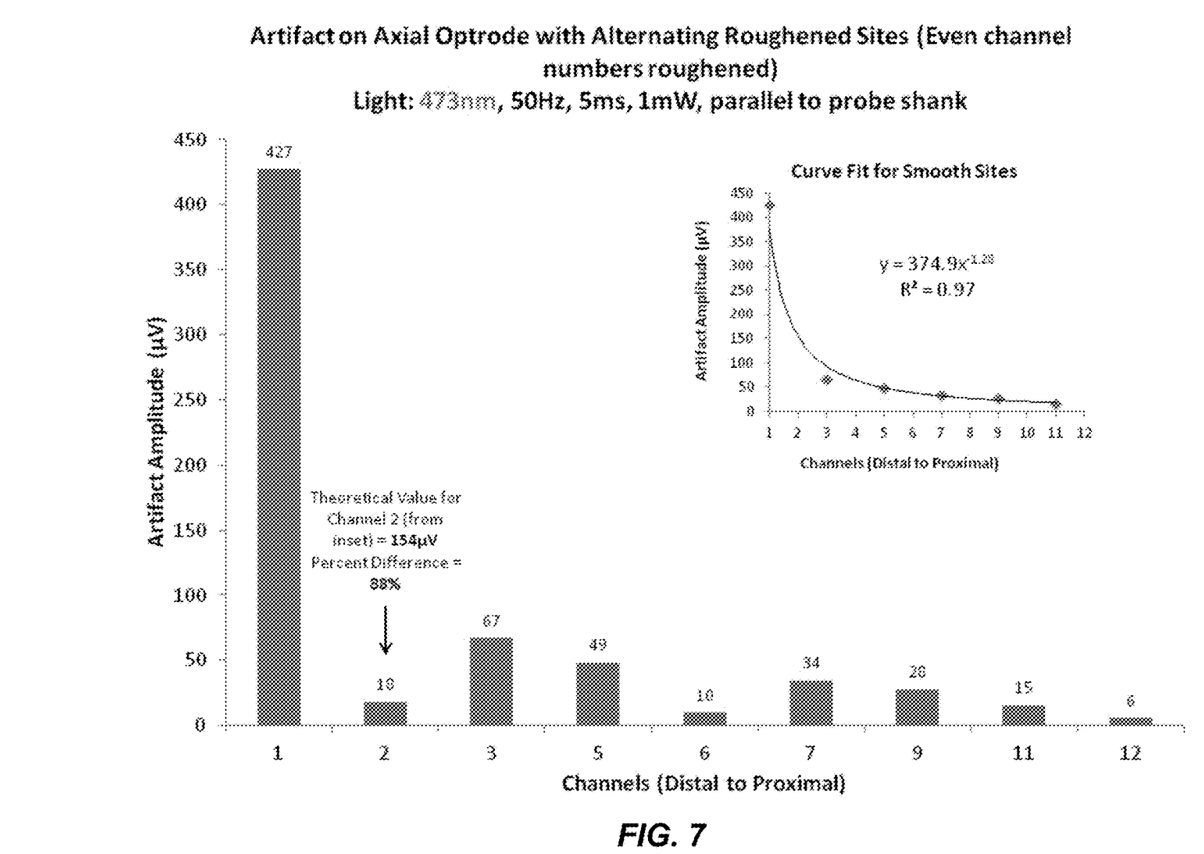
FIG. 7 shows the level of photoelectrochemical artifact on a series of recording electrodes in which only the even-numbered electrodes are roughened, using 473 nm light applied parallel to the probe shank.
Figure 8:
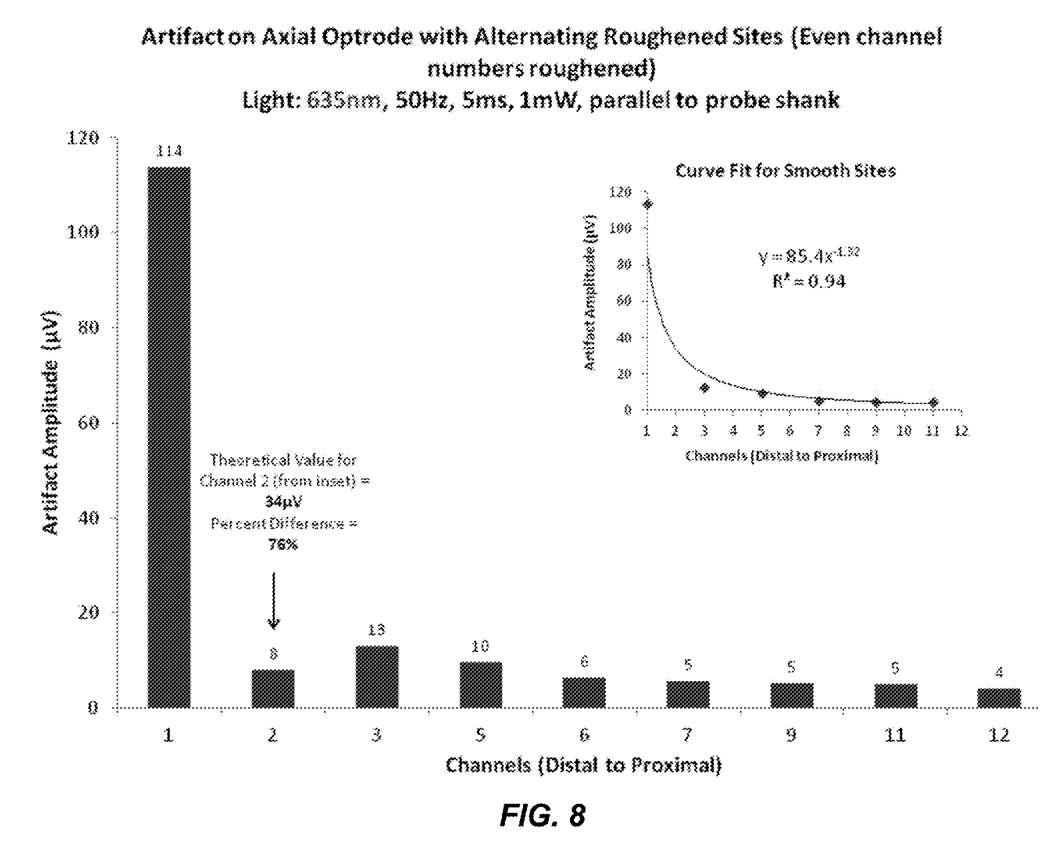
FIG. 8 shows the level of photoelectrochemical artifact on a series of recording electrodes in which only the even-numbered electrodes are roughened, using 635 nm light applied parallel to the probe shank.

In still another example, the even-numbered electrodes in a linear array, consisting of platinum, were patterned with nanoscale platinum structures to roughen the surface of even-numbered sites (FIG. 7). Light (473 nm, 50 Hz, 5 ms, 1 mW) was applied parallel to the probe shank containing the linear array, closest to electrode number 1. As shown in FIG. 7, the level of artifact on the even-numbered electrodes (only values for electrodes 2, 6, and 12 are shown) is greatly reduced compared to the uncoated electrodes. For electrode 2 the artifact is reduced by 90% compared to the predicted level of artifact for that electrode after accounting for spreading and scattering (FIG. 7, inset). Similar results were obtained when the electrode was illuminated under similar conditions but with 635 nm light (FIG. 8). In this case, the artifact for electrode 2 was reduced by 78% compared to the modeled correction for scattering and spreading (FIG. 8, inset).

Figure 9:
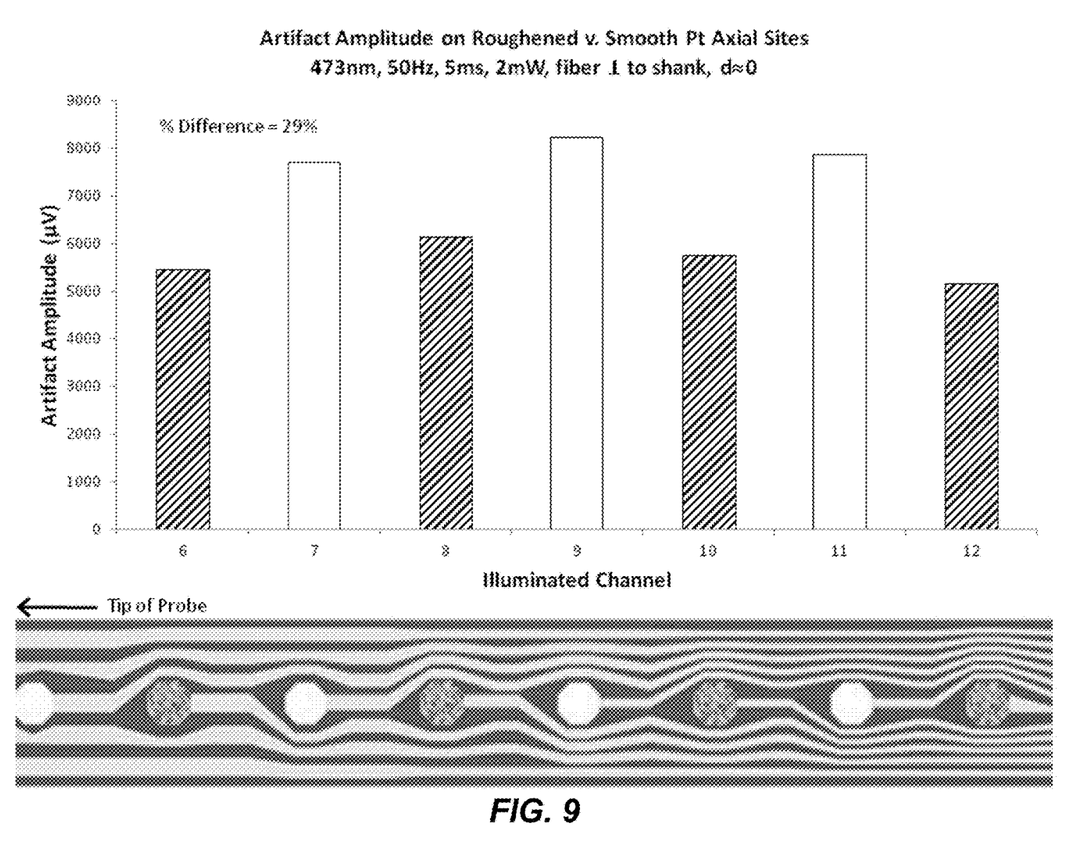
FIG. 9 shows the level of photoelectrochemical artifact on a series of recording electrodes in which only the even-numbered electrodes are roughened, using 473 nm light applied perpendicular to the probe shank.

In yet another example, an optical electrode in which the even-numbered electrodes were roughened was illuminated with light (473 nm, 50 Hz, 5 ms, 2 mW) perpendicular to the shank of the electrode with the light source being essentially adjacent to the electrodes (d≈0; FIG. 9). The roughened even-numbered electrodes showed a 29% decrease in artifact on average compared to the uncoated (smooth) odd-numbered electrodes.

Figure 10:
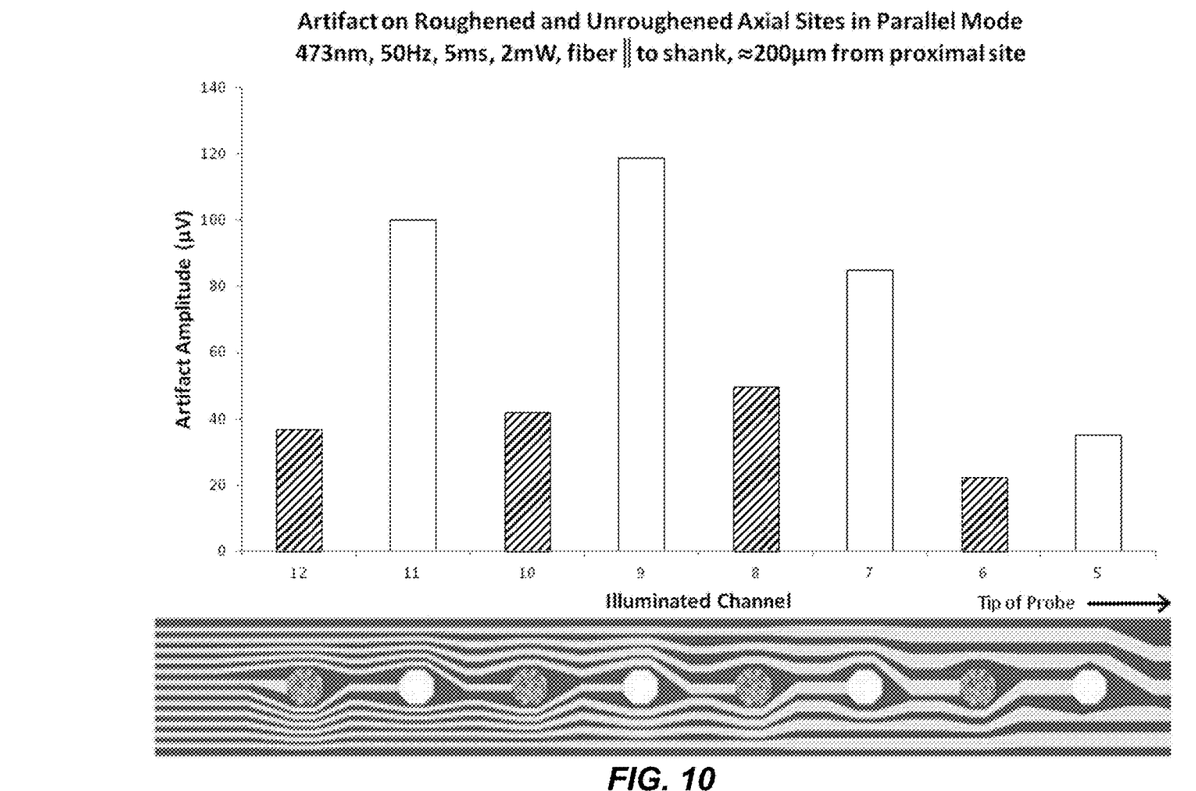
FIG. 10 shows the level of photoelectrochemical artifact on a series of recording electrodes in which only the even-numbered electrodes are roughened, using 473 nm light applied parallel to the probe shank and at a distance of 200 µm from the leftmost electrode.
Figure 11:
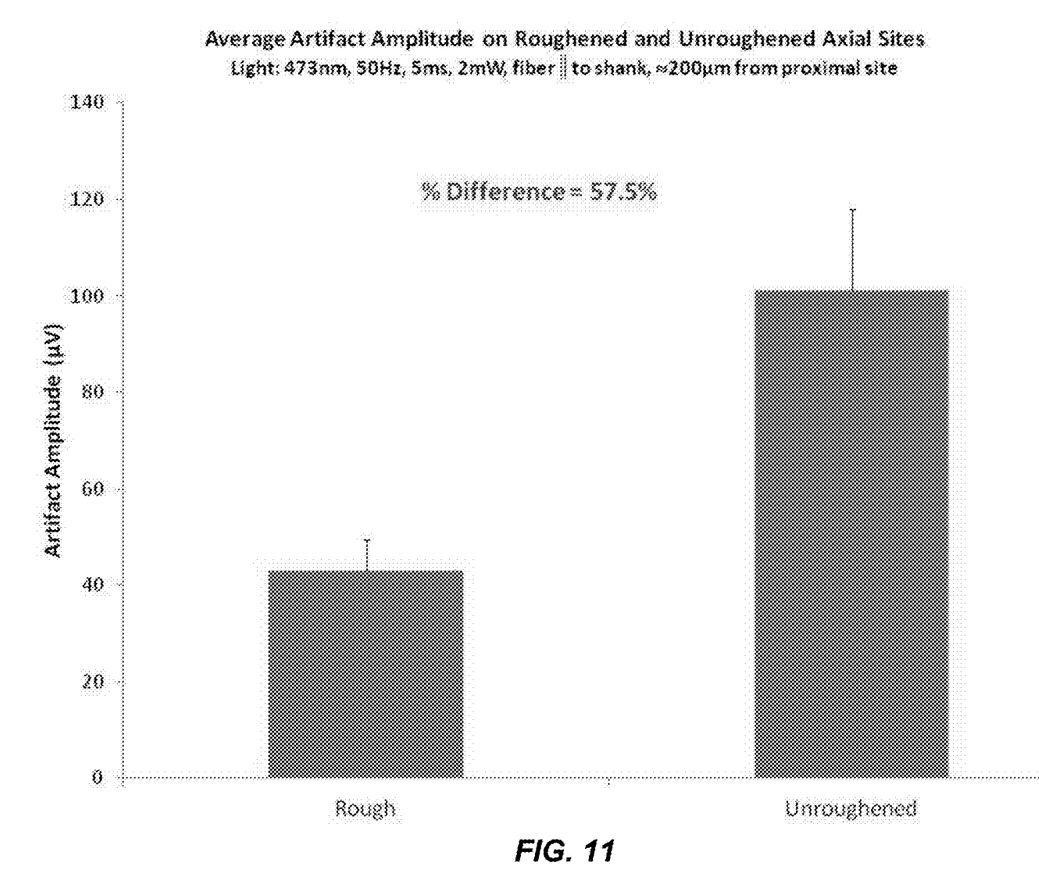
FIG. 11 shows a bar graph depicting the average photoelectrochemical artifact amplitude from FIG. 10 of the roughened and unroughened electrodes.
Figure 12:
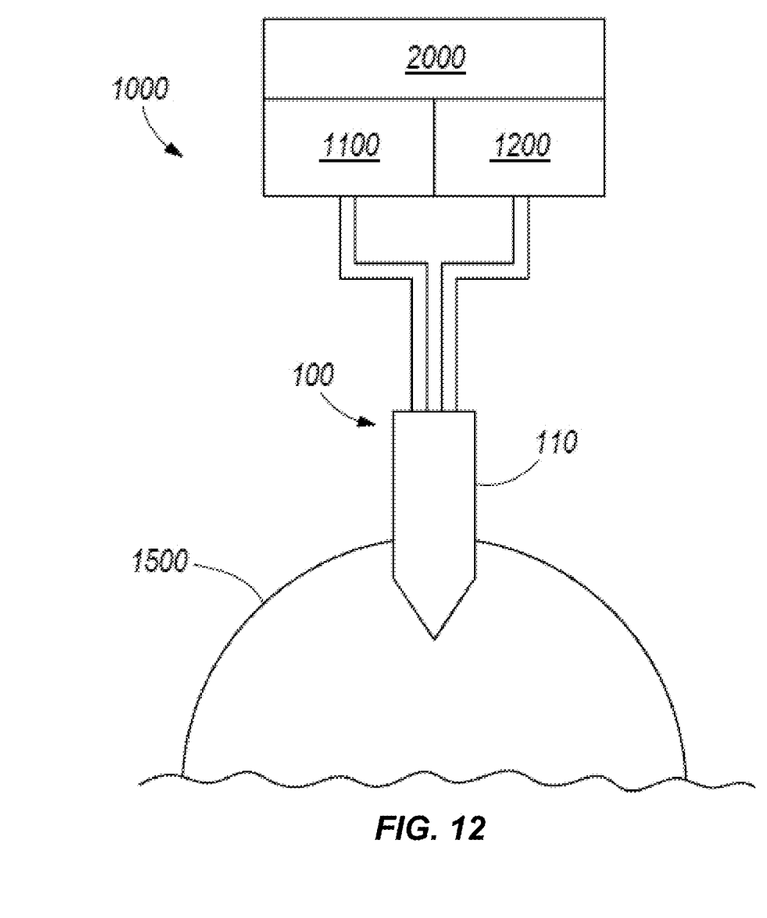
FIG. 12 shows an embodiment of a system for use with embodiments of the disclosed optical electrode.

FIG. 10 shows the artifact amplitude for an optical electrode with a linear array of recording electrodes in which the even-numbered recording electrodes are roughened. Light (473 nm, 50 Hz, 5 ms, 2 mW) is applied parallel to the shank of the optical electrode using an optical fiber placed at approximately 200 µm from the proximal recording electrode (i.e. 200 µm to the left of electrode 12 in the diagram of FIG. 10). Under these conditions, there is an average of 57.5% reduction in the photoelectrochemical artifact observed with the roughened recording electrodes compared to the unroughened/uncoated (smooth) electrodes (FIG. 11).

Thus, the invention provides, among other things, an optical electrode and a method of producing an optical electrode. Various features and advantages of the invention are set forth in the following claims.

What is claimed is:

1. An optical electrode device, comprising:
   a) a carrier;
   b) a plurality of electrodes supported on the carrier, at least one of which is a recording electrode configured to sense electrical signals from tissue, wherein the recording electrode comprises:
      i) an electrically conductive material selected from the group consisting of gold, platinum, iridium, platinum-iridium, titanium nitride, and iridium oxide; and
      ii) a roughened external material having a back side attached to the electrically conductive material to thereby provide the recording electrode with a roughened external surface forming a front side of the roughened external material, wherein the roughened external material is selected from the group consisting of PEDOT/PSS (poly(3,4-ethylene-dioxythiophene)/poly(styrene sulfonate), iridium oxide, glass nanospheres, glass microspheres, poly-styrene nanospheres, and poly-styrene microspheres, and
      iii) wherein the roughened external surface of the recording electrode has an average roughness as an arithmetic average of absolute values of a series of maximum and minimum vertical height measurements in nm on the roughened external surface that is greater than 10 nm; and
   c) a light source supported by the carrier, the light source configured to emit light that is directed at the roughened external surface of the recording electrode.

2. The optical electrode device of claim 1, wherein the roughened external surface of the recording electrode has an average roughness greater than 20 nm.

3. The optical electrode device of claim 1, wherein the roughened external surface of the recording electrode has an average roughness greater than 100 nm.

4. The optical electrode device of claim 1, wherein the roughened external surface of the recording electrode has a root mean square (RMS) surface roughness greater than 100 nm.

5. The optical electrode device of claim 1, wherein the plurality of electrodes are part of a thin-film structure.

6. The optical electrode device claim 1, wherein the light source comprises a waveguide.

7. A method of producing an optical electrode with a reduced photoelectrochemical artifact, comprising the steps of:
   a) providing a carrier;
   b) supporting a plurality of electrodes on the carrier, wherein at least one of the electrodes is configured as a recording electrode comprising:
      i) an electrically conductive material selected from the group consisting of gold, platinum, iridium, platinum-iridium, titanium nitride, and iridium oxide; and
      ii) a roughened external material having a back side attached to the electrically conductive material to thereby provide the recording electrode with a roughened external surface forming a front side of the roughened external material, wherein the roughened external material is selected from the group consisting of PEDQT/PSS (poly(3,4-ethylene-dioxythiophene)/poly(styrene sulfonate), iridium oxide, glass nanospheres, glass microspheres, poly-styrene nanospheres, and poly-styrene micro spheres;
   c) supporting a light source on the carrier, and configuring the light source to emit light that is directed at the roughened external surface of the recording electrode,
   d) wherein the roughened external surface of the recording electrode has an average roughness as an arithmetic average of absolute values of a series of maximum and minimum vertical height measurements in nm on the roughened external surface of the recording electrode that is greater than 10 nm.

8. The method of claim 7, including providing the roughened externs surface of the recording electrode having an average roughness of greater than 20 nm.

9. The method of claim 7, including providing the roughened external surface of the recording electrode having an average roughness of greater than 100 nm.

10. The method of claim 7, including providing the roughened external surface of the recording electrode having a root mean square surface roughness of greater than 100 nm.

11. The method of claim 7, including providing the plurality of electrodes comprising part of a thin-film structure.

12. The method of claim 7, including providing the light source comprising a waveguide.

13. The optical electrode device of claim 1, further comprising:
   a) an electrical subsystem in electrical communication with the plurality of electrodes; and
   b) an optical subsystem in electrical communication with the light source.

14. The optical electrode device of claim 1, wherein the light source is configured to emit light that impinges on the roughened external surface of the recording electrode at an angle that is less than normal.

15. The optical electrode device of claim 14, wherein the emitted light is substantially parallel to the roughened external surface of the recording electrode.

16. The optical electrode device of claim 1, wherein the roughened external surface of the recording electrode has a pattern selected from the group consisting of grooves, cross-hatching, regularly-spaced protrusions, regularly-spaced depressions, and combinations thereof.

17. An optical electrode device, comprising:
a) a carrier;
b) a plurality of electrodes supported on the carrier, wherein:
   i) at least one of the electrodes is a stimulation electrode configured to provide electrical stimulation to tissue, and wherein the stimulation electrode has an unroughened external surface with an average roughness that is less than 10 nm; and
   ii) at least one of the electrodes is a recording electrode configured to sense electrical signals from tissue, and wherein the recording electrode has a roughened external surface comprising:
   A) an electrically conductive material selected from the group consisting of gold, platinum, iridium, platinum-iridium, titanium nitride, and iridium oxide; and
   B) a roughened external material having a back side attached to the electrically conductive material to thereby provide the recording electrode with a roughened external surface forming a front side of the roughened external material, wherein the roughened external material is selected from the group consisting of PEDOT/PSS (poly(3,4-ethylene-dioxythiophene)/poly(styrene sulfonate), glass nanospheres, glass microspheres, poly-styrene nanospheres, and poly-styrene microspheres, and
   C) wherein the roughened external surface of the recording electrode has an average roughness as an arithmetic average of absolute values of a series of maximum and minimum vertical height measurements in nm on the roughened external surface of the recording electrode that is greater than 10 nm; and
c) a light source supported by the earner, the light source configured to emit light that is directed at the roughened external surface of the recording electrode.

* * * * *

UNITED STATES PATENT AND TRADEMARK OFFICE
CERTIFICATE OF CORRECTION

PATENT NO. : 9,782,091 B2
APPLICATION NO. : 13/557516
DATED : October 10, 2017
INVENTOR(S) : John P. Seymour et al.

It is certified that error appears in the above-identified patent and that said Letters Patent is hereby corrected as shown below:

In the Claims

Column 9, Line 5 Claim 8, delete "externs" and insert --external--.

Signed and Sealed this
Fifth Day of December, 2017

Joseph Matal
*Performing the Functions and Duties of the
Under Secretary of Commerce for Intellectual Property and
Director of the United States Patent and Trademark Office*